(12) United States Patent
Li

(10) Patent No.: US 6,647,191 B2
(45) Date of Patent: Nov. 11, 2003

(54) OPTICAL FIBER WITH LARGE EFFECTIVE AREA, LOW DISPERSION AND LOW DISPERSION SLOPE

(75) Inventor: Ming Jun Li, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 70 days.

(21) Appl. No.: 09/900,340

(22) Filed: Jul. 6, 2001

(65) Prior Publication Data

US 2002/0044755 A1 Apr. 18, 2002

Related U.S. Application Data

(60) Provisional application No. 60/225,728, filed on Aug. 16, 2000.

(51) Int. Cl.[7] ................................................ G02B 6/02
(52) U.S. Cl. ...................................................... 385/127
(58) Field of Search ................................ 385/123, 124, 385/125, 126, 127, 128, 141

(56) References Cited

U.S. PATENT DOCUMENTS

| 4,852,968 | A | 8/1989 | Reed ........................ 350/96.33 |
| 5,721,800 | A | 2/1998 | Kato et al. .................. 385/127 |
| 5,781,684 | A | 7/1998 | Liu ............................. 385/124 |
| 5,852,701 | A | 12/1998 | Kato et al. .................. 385/127 |
| 5,878,182 | A | 3/1999 | Peckham ..................... 385/123 |
| 5,905,838 | A | 5/1999 | Judy et al. .................. 385/123 |
| 6,072,929 | A | 6/2000 | Kato et al. .................. 385/123 |
| 6,266,467 | B1 | 7/2001 | Kato et al. .................. 385/123 |
| 6,459,839 | B1 | 10/2002 | Sauvageon et al. |
| 2001/0006572 | A1 | 7/2001 | Kato et al. .................. 385/123 |
| 2001/0022883 | A1 | 9/2001 | Montmorillon et al. ..... 385/123 |

FOREIGN PATENT DOCUMENTS

| DE | 198 39 870 A1 | 9/2000 | ............ G02B/6/18 |
| EP | 0774676 A2 | 5/1997 | ............ G02B/6/16 |
| EP | 0909964 A1 | 4/1999 | ............ G02B/6/16 |
| EP | 0 992 818 | 4/2000 | ............ G02B/6/16 |
| EP | 1 030 199 | 8/2000 | ............ G02B/6/16 |
| EP | 1 103 830 | 5/2001 | ............ G02B/6/16 |
| EP | 1 189 082 | 3/2002 | ............ G02B/6/22 |
| WO | WO 98/04941 | 2/1998 | ............ G02B/6/22 |
| WO | WO 00/17680 | 3/2000 | ............ G02B/6/16 |
| WO | WO 00/17681 | 3/2000 | ............ G02B/6/16 |
| WO | WO 00/17682 | 3/2000 | ............ G02B/6/16 |
| WO | WO 00/19255 | 4/2000 | ............ G02B/6/22 |
| WO | WO 00/20905 | 4/2000 | ............ G02B/6/16 |
| WO | WO 02/16970 | 2/2002 | |
| WO | WO 02/19576 | 3/2002 | ............ H04B/10/18 |

OTHER PUBLICATIONS

H. Hatayama et al, "Dispersion flattened fiber with large-effective-core area more than 50 $\mu m^2$", OFC '98 Technical Digest, pp. 304–305.

Lucent Technologies, "True Wave® RS Nonzero–Dispersion Optical Fiber", Copyright 1998.

Primary Examiner—Jean F. Duverne
(74) Attorney, Agent, or Firm—William J. Chervenak; Joseph M. Homa

(57) ABSTRACT

A single mode optical waveguide fiber having a relatively large effective area and a low dispersion slope has a segmented core having a central segment, a first annular segment, and a second annular segment. Each segment has a relative refractive index percent, and an inner and outer radius. The relative refractive index percent and the radii of each core segment are chosen from the following ranges: the relative index of the central segment within the range of about 0.53% to about 0.9%; the relative index of the first annular segment within the range of about −0.2% to about 0.15%; the relative index of the second annular segment within the range of about 0.1% to about 0.4%; the outer radius of the central segment within the range of about 3.1 $\mu m$ and about 5.0 $\mu m$; and the center radius of the third annular segment within the range of about 6.18 $\mu m$ and about 7.7 $\mu m$.

29 Claims, 2 Drawing Sheets

OPTICAL FIBER WITH LARGE EFFECTIVE AREA, LOW DISPERSION AND LOW DISPERSION SLOPE

This application claims the benefit of and priority to U.S. Provisional Patent Application No. 60/225,728, filed Aug. 16, 2000.

BACKGROUND OF THE INVENTION

1. Field of the Invention

The invention is directed to a single mode optical waveguide fiber for use in telecommunication systems and more particularly, a waveguide fiber which has a large effective area to reduce non-linear effects, and combine bend resistance, low attenuation, low dispersion, and low dispersion slope.

2. Technical Background

Optical amplifier technology and dense wavelength division multiplexing (DWDM) techniques are typically required in numerous telecommunication systems, such as those systems that require high power transmissions for long distances, as well as in metropolitan area networks.

With respect to high power transmissions for long distances, the definition of high power and long distances is meaningful only in the context of a particular telecommunication system wherein a bit rate, a bit error rate, a multiplexing scheme, and perhaps optical amplifiers are specified. There are additional factors, known to those skilled in the art, which have impact upon the meaning of high power and long distance. However, for most purposes, high power is an optical power greater than about 10 mW. In some applications, single power levels of 1 mW or less are still sensitive to non-linear effects, so that the effective area is still an important consideration in such lower power systems. A long distance is one in which the distance between electronic regenerators can be in excess of 100 km. The regenerators are to be distinguished from repeaters which make use of optical amplifiers. Repeater spacing, especially in high data density systems, can be less than half the regenerator spacing. To provide a suitable waveguide for a multiplex transmission, the total dispersion should be low, but not zero, and have a low slope over the window of operating wavelength.

Generally, an optical waveguide fiber having a large effective area, $A_{eff}$, reduces non-linear optical effects, including self phase modulation, four wave mixing, cross phase modulation, and non-linear scattering processes, all of which can cause degradation of signals in high powered systems. A waveguide fiber having a segmented core can generally provide a large effective area while limiting the non-linear optical effects.

The mathematical description of these non-linear effects includes the ratio, $P/A_{eff}$, where P is the optical power. For example, a non-linear optical effect can be described by an equation containing a term, $\exp[P \times L_{eff}/A_{eff}]$, where $L_{eff}$ is effective length. Thus, an increase in $A_{eff}$ produces a decrease in the non-linear contribution to the degradation of a light signal. A core having multiple segments each characterized by a refractive index profile, a relative index, and a radius, meets many of the desired functional properties.

The requirement in the telecommunication industry for greater information capacity over long distances, without electronic signal regeneration, has led to a reevaluation of single mode fiber index profile design. The focus of this reevaluation has been to provide optical waveguides which:

reduce non-linear effects such as those noted above;
are optimized for the lower attenuation operating wavelength range around 1550 nm;
are compatible with optical amplifiers; and,
retain the desirable properties of waveguides such as high strength, fatigue resistance, and bending resistance.

A suitable waveguide fiber must have low linear dispersion and low attenuation as well. In addition, the waveguide fiber must display these properties over a particular extended wavelength range in order to accommodate wavelength division multiplexing used for multiple channel transmission.

As noted above, dense wavelength-division multiplexing technology is used within metropolitan area networks to meet the increasing demand for bandwidth to allow more channels to operate within a single fiber, as well as to allow the transfer of single transmissions requiring significant amounts of bandwidth, such as multimedia files and applications. DWDM technology requires new fiber designs with low finite dispersion across the entire WDM window to improve system performance and reduce system costs.

Standard-single mode fibers currently in use in metropolitan area networks typically exhibit a dispersion of near 17 ps/nm-km in the 1550 nm operating window. Therefore, dispersion compensation is needed for a WDM system having a bit rate of 2.5 Gb/s or higher. Dispersion compensation increases system cost and can result in an attenuation penalty. It would be desirable to design an optical fiber that exhibits a lower dispersion than that currently available in both the 1300 nm and 1550 nm operating windows.

Waveguide designs which also are relatively easy to manufacture and which permit management of dispersion are favored, because of their low cost and added flexibility. The designs described herein are well suited to a dispersion managing strategy in which the waveguide dispersion is varied along the waveguide fiber length to toggle the total dispersion between positive and negative values.

U.S. Pat. No. 5,781,684 incorporated herein by reference as though fully set forth in its entirety, discloses and describes segmented core waveguide fibers having large effective areas. A feature of the segmented core of the waveguide fiber disclosed in the '684 patent is that at least one of the segments has a negative or a relative refractive index. The present application discloses and describes segmented core waveguide fibers that provide a unique set of functional properties.

SUMMARY OF THE INVENTION

This invention meets the need for a single mode optical waveguide fiber that offers the benefits of a relatively large effective area together with a substantially flat dispersion slope over an extended operating range.

The invention relates to a single mode optical waveguide fiber including a segmented core. Each of the segments is described by a refractive index profile, a relative refractive index percent, and an inner and outer radius. The optical waveguide fiber further includes a clad layer surrounding and in contact with the core, and having a refractive index profile.

In a preferred embodiment, the index profiles are further selected to provide a dispersion slope of less than about 0.07 ps/nm²-km. A further embodiment has a dispersion slope of equal to or less than about 0.057 ps/nm²-km while maintaining a bending induced loss on the pin array test of less than about 6 dB and preferably less than 0.68 dB.

In addition, embodiments having induced attenuation loss due to lateral load bending less than 0.25 dB/m and preferably less than 0.208 dB/m are disclosed and described.

Reference will now be made in detail to the present preferred embodiments of the invention, examples of which are illustrated in the accompanying drawings. Exemplary embodiment of the segmented core refractive index profile of the present invention is shown in each of the figures.

DETAILED DESCRIPTION OF THE PREFERRED EMBODIMENT

Figure 1:
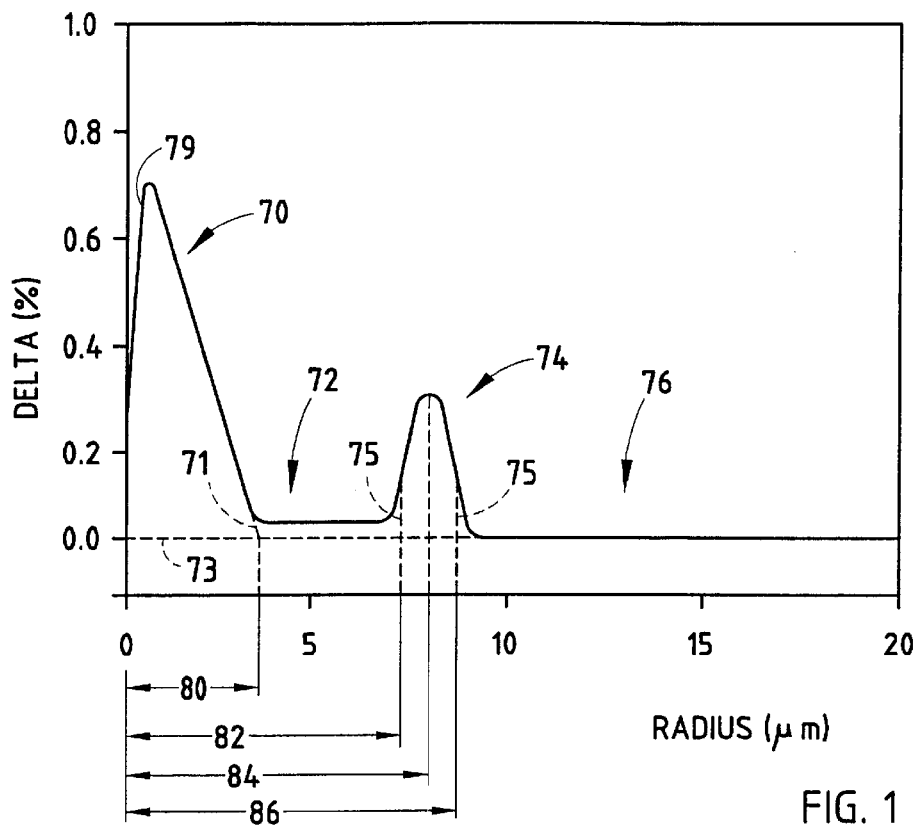
FIG. 1 is a diagram of a waveguide fiber refractive index profile of an optical waveguide having a three-segment core and a positive relative index in each and every core segment.

Additional features and advantages of the invention will be set forth in the detailed description which follows and will be apparent to those skilled in the art from the description or recognized by practicing the invention as described in the description which follows together with the claims and appended drawings.

It is to be understood that the foregoing description is exemplary of the invention only and is intended to provide an overview for the understanding of the nature and character of the invention as it is defined by the claims. The accompanying drawings are included to provide a further understanding of the invention and are incorporated and constitute part of this specification. The drawings illustrate various features and embodiments of the invention which, together with their description serve to explain the principals and operation of the invention.

Definitions

The following definitions are commonly used in the art. The radii of the segments of the core are defined in terms of the index of refraction of the material of which the segment is made. A particular segment has a first and a last refractive index point. A central segment has an inner radius of zero because the first point of the segment is on the center line. The outer radius of the central segment is the radius drawn from the waveguide center line to the last point of the refractive index of the central segment. For a segment having a first point away from the center line, the radius from the waveguide center line to the location of its first refractive index point is the inner radius of that segment. Likewise, the radius from the waveguide center line to the location of the last refractive index point of the segment is the outer radius of that segment.

The segment radii may be conveniently defined in a number of ways. In this application, radii are defined in accord with the figures, described in detail below. The definitions of segment radius and refractive index, used to describe refractive index profile, in no way limit the invention. Definitions are given herein because in carrying out model calculations, the definitions must be used consistently. The model calculations set forth in the tables below are made using the geometrical definitions labeled in the figures and described in the detailed description.

The effective area is generally defined as, $$A_{eff}=2\pi(\int E^2\ r\ dr)^2/(\int E^4\ r\ dr),$$

wherein the integration limits are zero to $\infty$, and E is the electric field associated with the propagated light.

The mode field diameter, $D_{mf}$, is measured using the Peterman II method wherein, $2w=D_{mf}$ and $w^2=(2\int E^2\ r\ dr/\int[dE/dr]^2\ r\ dr)$, the intergral limits being 0 to $\infty$.

The relative index of a segment, $\Delta\%$, as used herein, is defined by the equation, $$\Delta\%=100\times(n_1-n_c)/n_c,$$

where $n_1$ is the maximum refractive index of the index profile segment denoted as i, and $n_c$, the reference refractive index, is taken to be the minimum index of the clad layer. Every point in the segment has an associated relative index. The maximum relative index is used to conveniently characterize a segment whose general shape is known.

The term refractive index profile or index profile is the relation between $\Delta\%$ or refractive index and radius over a selected segment of the core.

The term alpha ($\alpha$) profile refers to a refractive index profile that may be expressed by the equation, $$n(r)=n_o(1-\Delta[r/a]^\alpha),$$

where r is core radius, $\Delta$ is defined above, a is the last point in the profile segment, the value of r at the first point of the $\alpha$-profile is chosen to accord with the location of the first point of the profile segment, and $\alpha$ is an exponent which defines the profile shape. Other index profiles include a step index, a trapezoidal index and a rounded step index, in which the rounding is usually due to dopant diffusion in regions of rapid refractive index change.

Total dispersion is defined as the algebraic sum of waveguide dispersion and material dispersion. Total dispersion is also referred to as chromatic dispersion in the art. The units of total dispersion are ps/nm-km.

A refractive index profile in general has an associated effective refractive index profile that is different in shape. An effective refractive index profile may be substituted, for its associated refractive index profile without altering the waveguide performance.

The bend resistance of a waveguide fiber is expressed as induced attenuation under prescribed test conditions. The bend test referenced herein is the pin array bend test that is used to compare relative resistance of waveguide fiber to bending. To perform the test, attenuation loss is measured for a waveguide fiber with essentially no induced bending loss. The waveguide fiber is then woven in a serpentine path through the pin array and attenuation again measured. The loss induced by bending is the difference between the two measured attenuation values. The pin array is a set of ten cylindrical pins arranged in a single row and held in a fixed position on a flat surface. The pin spacing is 5 mm, center to center, and the pin diameter is 0.67 mm. During testing, sufficient tension is applied to make the serpentine woven waveguide fiber conform to the portions of the pin surface at which there is contact between the pin and the fiber.

The segmented core optical waveguide described and disclosed herein has a generally segmented core. Each of the segments is described by a refractive index profile, relative refractive index percent, $\Delta_i\%$, and an outside radius, $r_i$. The subscript i on r and $\Delta$ refers to a particular segment. The segments are numbered 1 through n beginning with the innermost segment which includes the waveguide long axis centerline. A clad layer having a refractive index of $n_c$ surrounds the core.

The radius, relative refractive index percent, and refractive index profile of each segment of the core are selected to provide: attenuation at 1550 nm no greater than 0.25 dB/km; zero dispersion wavelength shorter than 1530 nm; a dispersion slope of less than about 0.07 ps/nm$^2$-km; effective area greater than 45 $\mu$m$^2$ at 1550 nm; and cut off wavelength of fiber in cabled form in less than about 1300 nm. The novel segmented core design of this application displays the required properties cataloged above.

A general representation of the alternative core refractive index profile is illustrated in FIG. 1, which shows relative refractive index percent chartered versus waveguide radius. Although FIG. 1 shows only three discrete segments, it is understood that the functional requirements may be met by forming a core having more than three segments. However, embodiments having fewer segments are usually easier to manufacture and are therefore preferred.

Index profile structure characteristic of the novel waveguide fiber is shown by core segments 70, 72 and 74 (FIG. 1) and are discussed in Example 1. The refractive index profile associated with each segment may be adjusted to reach a core design which provides the required waveguide fiber properties.

Figure 2:
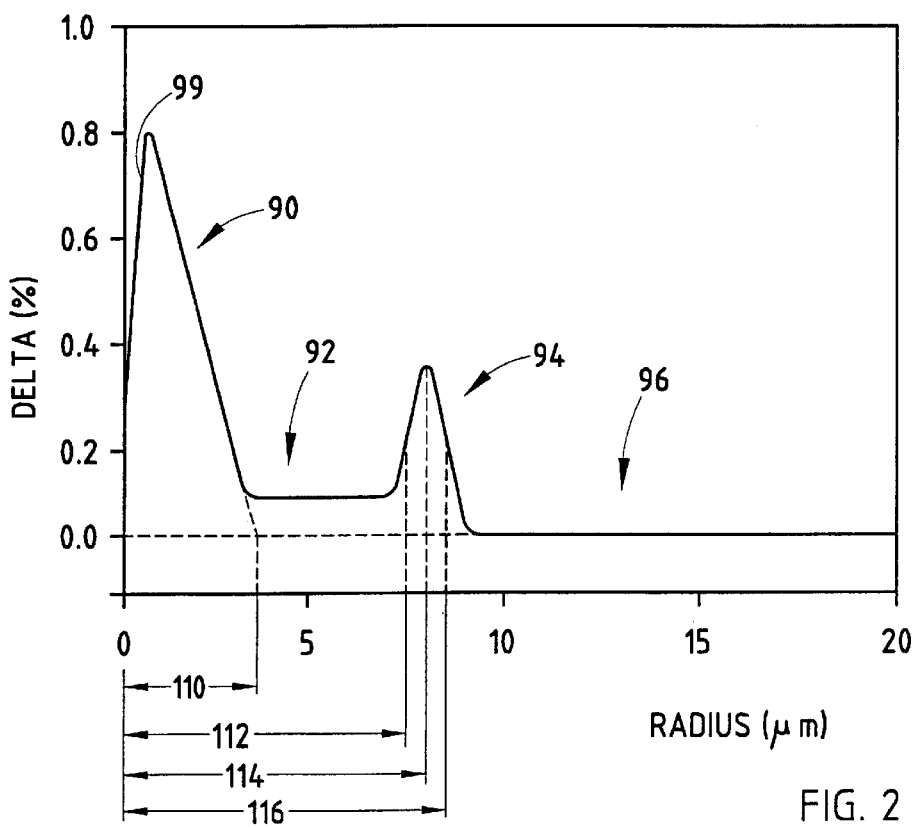
FIG. 2 is a diagram of a waveguide fiber refractive index profile of an optical waveguide having a three-segment core and a positive relative index in each and every core segment.
Figure 3:
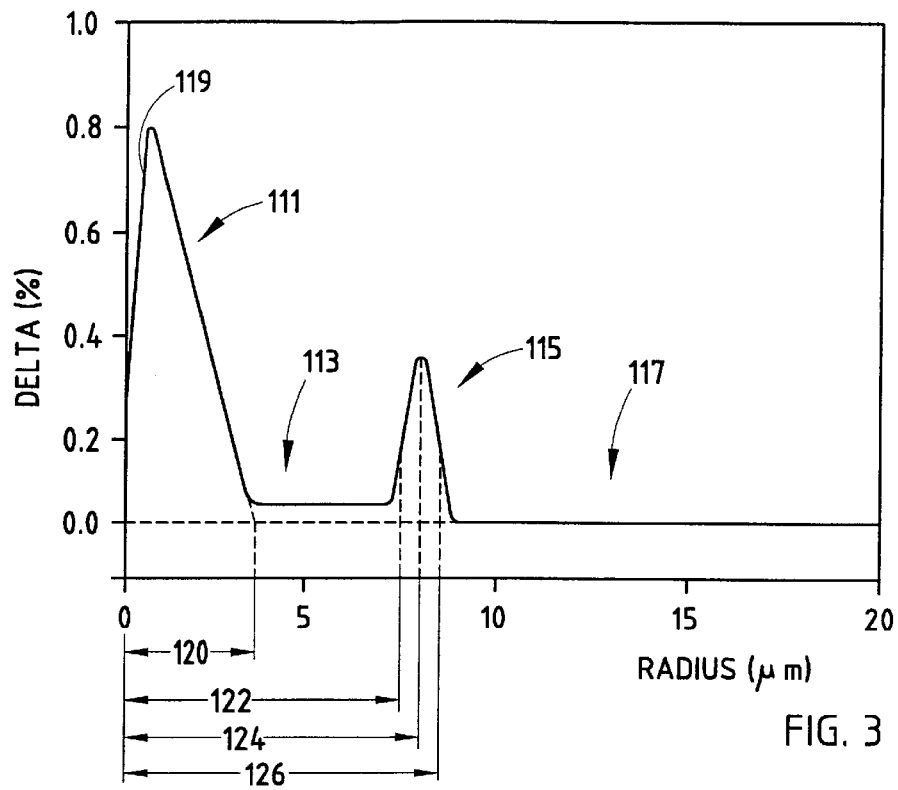
FIG. 3 is a diagram of a waveguide fiber refractive index profile of an optical waveguide having a three-segment core and a positive relative index in each and every core segment.

FIGS. 2 and 3 illustrate embodiments of the novel waveguide fiber core design. The waveguide fiber illustrated in FIG. 2 includes core segments 90, 92 and 94. The waveguide fiber illustrated in FIG. 3 includes core segments 110, 112 and 114. The properties associated with each of these embodiments are discussed in Examples 2 and 3, respectively.

Figure 4:
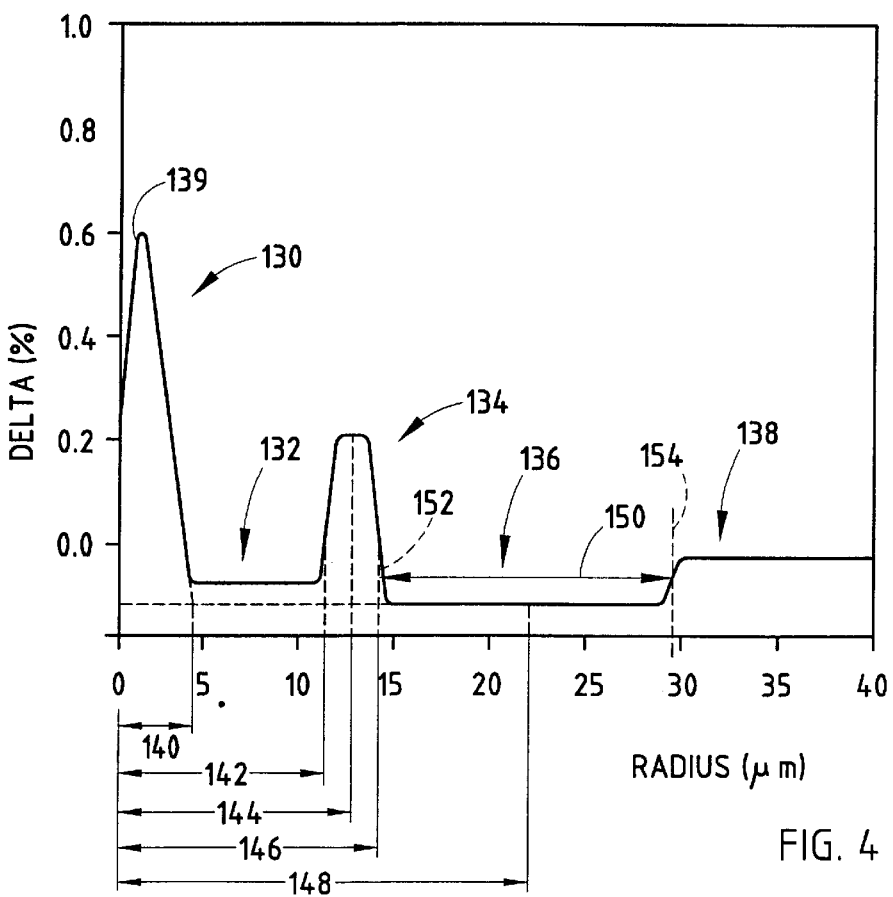
FIG. 4 is a diagram of the waveguide fiber refractive index profile of an optical waveguide having a four-segment core and a negative relative index in the first and third annular segments.

FIG. 4 illustrates yet another embodiment of the novel waveguide fiber core design. In this case, the core is provided a first, second, third and fourth segment 130, 132, 134 and 136, respectively. The properties associated with the fourth embodiment are discussed in Example 4.

It should be noted that lines 76, 96, 117, and 138 in the respective FIGS. 1–4, represent the refractive index of the cladding which is used to calculate the $\Delta$%'s characteristic of the segments. Further, the rounding of the corners of the step profiles of FIGS. 1–4, as well as the center line refractive index depressions 79, 99, 119 and 139 may be due to diffusion of dopant during manufacturing of waveguide fiber. It is possible, but often not necessary to compensate, for example, in the doping step, for such diffusion.

EXAMPLE 1

The diagram of FIG. 1 is an embodiment of the novel waveguide core having three segments 70, 72, and 74, and an inner cladding 76. The central core or first segment 70 has a relative index, $\Delta_1$%, within the range of about 0.667% to about 0.815%, and more preferably of about 0.741%, and an outer radius 80, $r_1$, within the range of about 3.299 $\mu$m to about 4.032 $\mu$m, and more preferably of about 3.665 $\mu$m. The first surrounding annular segment or second segment 72 has a relative index, $\Delta_2$%, within the range of about 0.023% to about 0.028% and more preferably of about 0.025%. The outer radius 80, $r_1$, of the central segment 70 is also the inner radius of the first annular segment 72. This convention will be used consistently in all of the examples and corresponding figures. The radius $r_1$, therefore, is the intersection of the central segment and the first annular segment. In this case, the intersection point is defined as the intersection of the extrapolated descending portion of the index profile of the central segment 70, represented by line 71, with the horizontal axis 73, defined as the axis through the most negative point or points of the refractive index profile.

The outer radius 82, $r_2$, of the first annular segment 72, is within the range of about 5.85 $\mu$m to about 7.15 $\mu$m and is more preferably 6.5 $\mu$m and is measured from the fiber centerline to the vertical line depending from the half maximum relative index point of the ascending portion of second annular segment 74. The half maximum point is determined using the clad layer as the reference index. The relative index of the clad layer is therefore zero. For example, in FIG. 1, second annular segment has a relative index $\Delta_3$% of about 0.3%, thus, relative to the $\Delta$%=0 of the clad layer, the magnitude is about 0.3%. Dashed vertical lines 75 depend from the 0.15% points, which are half of the magnitude of $\Delta_3$%. The center radius 84 of the second annular segment is within the range of about 6.3 $\mu$m to about 7.7 $\mu$m and is more preferably about 7.0 $\mu$m, while the outer radius, $r_3$, 86 of the second annular segment is within the range of about 6.93 $\mu$m to about 8.47 $\mu$m and is more preferably about 7.5 $\mu$m. The width of the second annular segment 74 is within the range of about 0.9 $\mu$m to about 1.1 $\mu$m and is more preferably about 1.0 $\mu$m. The relative index, $\Delta_c$%, of the inner cladding is about 0.1%.

The properties of the waveguide fiber of FIG. 1, calculated using a computer model, are given in Table 1.

TABLE 1

| | |
|---|---|
| Zero-dispersion wavelength (nm) | 1490.0 |
| Dispersion slope (ps/nm$^2$-km) | 0.0673 |
| Mode field diameter ($\mu$m) | 8.6 |
| Effective area ($\mu$m$^2$) | 54.9 |
| Cable cutoff wavelength (nm) | 1082 |
| Pin array bending loss (dB/km) | 2.98 |
| Lateral load bending loss (dB/m) | 0.136 |

In this example, the effective area is about 55 $\mu$m$^2$, the pin array bend loss is about 2.98 dB/km, and the attenuation of the resultant waveguide is about 0.186 dB/km.

EXAMPLE 2

Another variation of the novel waveguide core having three segments, including a central core or first segment 90, a first annular or second segment 92, and a second annular or third segment 94, is shown in FIG. 2. In this example, each and every core segment has a positive relative index. More specifically, central core segment 90 has a positive relative index, $\Delta_1$%, within the range of about 0.722% to about 0.882% and is more preferably about 0.802%, first annular segment has a positive relative index, $\Delta_2$%, of within the range of about 0.052% to about 0.064% and is more preferably about 0.058%, and second annular segment 94 has a positive relative index, $\Delta_3$%, of within the range of about 0.240% to about 0.294% and is more preferably about 0.267%. The inner cladding 96 has a relative index, $\Delta_c$%, of 0%.

The radii for the core segments of the third embodiment are calculated in accordance with the conventions discussed above. Central core 90 has an outer radius 110, $r_1$, within the range of about 3.159 $\mu$m to about 3.861 $\mu$m and is more preferably about 3.510 $\mu$m. First annular segment 92 has an outer radius 112, $r_2$, within the range of about 5.783 $\mu$m to about 7.068 $\mu$m and is more preferably about 6.425 $\mu$m. Second annular segment 94 has a central radius 114 within the range of about 6.183 $\mu$m to about 7.557 $\mu$m and is more preferably about 6.870 $\mu$m and an outer radius 116, $r_2$, of within the range of about 6.584 $\mu$m to about 8.047 $\mu$m and is more preferably about 7.315 $\mu$m.

Table 2 sets forth the calculated properties of the FIG. 2 refractive index profile.

TABLE 2

| | |
|---|---|
| Zero-dispersion wavelength (nm) | 1489 |
| Dispersion slope (ps/nm²-km) | 0.0676 |
| Mode field diameter (μm) | 8.3 |
| Effective area (μm²) | 50.8 |
| Cable cutoff wavelength (nm) | 1121 |
| Pin array bending loss (dB/km) | 0.68 |
| Lateral load bending loss (dB/m) | 0.097 |

In example 2, the effective area is about 51 μm², the pin array bending loss is about 0.68 dB/km, and the lateral load bending loss is about 0.097 dB/m.

EXAMPLE 3

Another variation of the novel three-segment waveguide core, includes a central core or first segment 111, a first annular or second segment 113, and a second annular or third segment 115. In this example, each and every core segment has a positive relative index. More specifically, central core segment 111 has a positive relative index, $\Delta_1\%$, within the range of about 0.716% to about 0.876% and is more preferably about 0.796%, first annular segment 113 has a positive relative index, $\Delta_2\%$, within the range of about 0.018% and 0.022% and is more preferably about 0.020%, and second annular segment 115 has a positive relative index, $\Delta3\%$, of within the range of about 0.265% to about 0.323% and is more preferably about 0.294%. The inner cladding 117 has a relative index, $\Delta_c\%$, of 0%.

The radii for the core segments of the third embodiment are calculated in accordance with the conventions discussed above. Central core 111 has an outer radius 120, $r_1$, of within the range of about 3.375 μm to about 4.125 μm and is more preferably about 3.750 μm. First annular segment 113 has an outer radius 122, $r_2$, of within the range of about 6.994 μm to about 8.548 μm and is more preferably about 7.771 μm. Second annular segment 115 has a central radius 124 of within the range of about 7.38 μm to about 7.7 μm and an outer radius 126, $r_2$, of within the range of about 7.766 μm to about 9.442 μm and is more preferably about 8.629 μm.

Table 3 sets forth the calculated properties of the FIG. 3 refractive index profile.

TABLE 3

| | |
|---|---|
| Zero-dispersion wavelength (nm) | 1480 |
| Dispersion slope (ps/nm²-km) | 0.0565 |
| Mode field diameter (μm) | 8.0 |
| Effective area (μm²) | 47.4 |
| Cable cutoff wavelength (nm) | 1006 |
| Pin array bending loss (dB/km) | 0.83 |
| Lateral load bending loss (dB/m) | 0.074 |

In example 3, the effective area is about 47.4 μm², the pin array bending loss is about 0.83 dB/km, and the lateral load bending loss is about 0.074 dB/m.

EXAMPLE 4

An alternative embodiment of the novel waveguide core has four segments, including a central segment 130, a second segment or first annular segment 132, a third segment or second annular segment 134, and a fourth segment or third annular segment 136, and is shown in FIG. 4. In this example, central segment 130 and second annular segment 134 each have a positive relative index, $\Delta_1\%$ and $\Delta_3\%$, respectively, and first annular segment 132 and the third annular segment 136 each have a negative relative index, $\Delta_2\%$ and $\Delta_4\%$, respectively. More specifically, central segment 130 has a relative index, $\Delta_1\%$ of within the range of about 0.531% to about 0.649% and is more preferably about 0.590%, first annual segment 132 has a relative index, $\Delta_2\%$ of within the range of about −0.083% to about −0.068% and is more preferably about −0.075%, second annular segment 134 has a relative index, $\Delta_3\%$, of within the range of about 0.190% to about 0.232% and is more preferably about 0.211%, and third annular segment 136 has a relative index of within the range of about −0.11% to about −0.09% and is more preferably about −0.1%. The inner cladding has a refractive index, $\Delta_c\%$, of 0%.

The radius 140, $r_1$, of the central segment 130 is within the range of about 3.682 μm to about 4.500 μm and is more preferably about 4.091 μm. The outer radius 142, $r_2$, of the first annular segment 132 is within the range of about 10.382 μm to about 12.690 μm and is more preferably about 11.536 μm. The center radius 144 of the second annular segment 134 is within the range of about 11.691 μm to about 14.289 μm and is more preferably about 12.990 μm, while the outer radius 144, $r_3$, for the second annular segment 134 is within the range of about 13.000 μm to about 15.888 μm and is more preferably about 14.444 μm.

For profiles having more than one annular segment, the outermost annular segment is characterized by a radius, $r_4$, 148 drawn from the centerline of the geometric center of the segment. The geometric center is determined by dividing in half the distance 150 between the vertical lines 152 and 154 drawn from the half magnitude relative index points of the index profiles bounding the outermost annular segment. Magnitude is measured from the horizontal line defined by the most negative $\Delta\%$, as described above. The distance 150 is the width of the third annular segment. In example 4, the outer radius 148, $r_4$, of the third annular segment is within the range of about 15.687 μm to about 19.173 and is more preferably about 17.43 μm.

Table 4 sets forth the calculated properties of the FIG. 4 refractive index profile.

TABLE 4

| | |
|---|---|
| Zero-dispersion wavelength (nm) | 1428 |
| Dispersion slope (ps/nm²-km) | 0.0405 |
| Mode field diameter (μm) | 8.7 |
| Effective area (μm²) | 55.5 |
| Cable cutoff wavelength (nm) | 1260 |
| Pin array bending loss (dB/km) | 3.4 |
| Lateral load bending loss (dB/m) | 0.114 |

In this example, the effective area is about 55.5 μm², the pin array bending loss is about 3.4 dB/km, and the lateral bending loss is about 0.114 dB/km.

The profiles of FIGS. 1–4 are members of a group of profiles that exhibit similar performance to that set forth in Tables 1–4. The group of refractive index profiles in accord with FIGS. 1–4 and that have substantially similar functional parameters have relative indexes in the respective ranges of about 0.53% to about 0.9% for the central segment, $\Delta_1\%$, of about −0.2% to about 0.15% for the first annular segment, $\Delta_2\%$, of about 0.1% to about 0.4% for the second annular segment, $\Delta_3\%$, and about −0.2% to about 0% for the third annular segment, $\Delta_4$. The corresponding radii of the group are in the respective ranges of about 3.1 μm to about 5.0 μm for the central segment outer radius, $r_1$, and about 6.18 μm to about 7.7 μm and about 11.691 μm to about 14.289 μm for the center radius of the second annular segment. The width of the second annular segment is within the range of about 0.43 μm to about 5.3 μm. These radii further correspond to an inner cladding radius within the range of about 25 μm to about 40 μm.

The refractive indices and the cross sectional profile of the fibers made according to the present invention can be accomplished using manufacturing techniques known to those skilled in the art.

It will become apparent to those skilled in the art that various modifications to the preferred embodiment of the invention as described herein can be made without departing from the spirit or scope of the invention as defined by the appended claims.

The invention claimed is:

1. A single mode optical wave guide fiber, comprising:
   a core region having a central segment, a first annular segment, a second annular segment, and a third annular segment, each of the segments having a relative refractive index percent, and an inner and outer radius; and
   a clad layer surround and in contact with the core, the clad layer having a relative refractive index percent; and
   wherein, the radius and relative refractive index percent and the radii of each segment are chosen from the following ranges:
      the relative index of the central segment within the range of from about 0.53% to about 0.9%;
      the relative index of the first annular segment within the range of from about −0.2% to about 0.15%;
      the relative index of the second annular segment within the range of from about 0.1% to about 0.4%;
      the relative index of the third annular segment within the range of from about −0.2% to about 0;
      the outer radius of the central segment within the range of from about 3.1 μm to about 5.0 μm;
      the center radius of the second annular segment within the range of from about 11.69 μm to about 14.3 μm; and
   the width of the second annular segment within the range of from about 0.43 μm to about 5.3 μm;
      wherein the radius and relative refractive index percent and the radii of each segment are chosen to yield a dispersion zero less than about 1490 nm; and
      wherein the fiber has a cabled cutoff less than or equal to about 1260 nm.

2. The single mode optical waveguide fiber of claim 1, wherein the outer radius of the third annual segment is within the range of from about 15.68 μm to about 19.2 μm.

3. The single mode optical waveguide fiber of claim 2, wherein the relative indices and radii are further selected to provide a dispersion slope within the optical waveguide fiber of less than about 0.07 ps/nm²-km.

4. The single mode optical waveguide fiber of claim 3, wherein the relative indices and radii are further selected to provide an effective area of greater than or equal to about 45 μm².

5. The single mode optical waveguide fiber of claim 4, wherein the relative indices and radii are further selected to provide a total dispersion at 1550 nm of less than or equal to about 5.0 ps/nm-km.

6. The single mode optical waveguide fiber of claim 5, wherein the relative indices and radii are further selected to provide an attenuation in the optical waveguide fiber is less than or equal to about 0.25 dB/km.

7. The single mode optical waveguide fiber of claim 6, wherein the relative indices and radii are further selected to provide a pin array bending loss is less than or equal to about 6 dB.

8. The single mode optical waveguide fiber of claim 1, wherein the relative indices and radii are further selected to provide an effective area of greater than or equal to about 45 μm².

9. The single mode optical waveguide fiber of claim 1, wherein the relative indices and radii are further selected to provide a total dispersion at 1550 nm of less than or equal to about 5.0 ps/nm-km.

10. The single mode optical waveguide fiber of claim 1, wherein the relative indices and radii are further selected to provide an attenuation in the optical waveguide fiber is less than or equal to about 0.25 dB/km.

11. The single mode optical waveguide fiber of claim 1, wherein the relative indices and radii are further selected to provide a pin array bending loss is less than or equal to about 6 dB.

12. The single mode optical waveguide fiber of claim 1, wherein at least two non-adjacent core segments have a refractive index that is positive, and at least two non-adjacent core segments have a refractive index that is negative.

13. A method for constructing a single mode optical waveguide fiber, comprising:
   forming a central core segment having a relative index within the range of from about 0.53% to about 0.9%, and an outer radius within the range of from about 3.1 μm to about 5.0 μm;
   forming a first annular core segment about the central core segment, the first annular core segment having a relative index within the range of from about −0.2% to about 0.15%; and
   forming a second annular core segment about the first annular core segment, the second annular core segment having a relative index within the range of from about 0.1% to about 0.4%, a center radius within the range of from about 6.18 μm to about 7.7 μm, and a width within the range of from about 0.4 μm to about 5.3 μm;
   wherein the radius and relative refractive index percent and the radii of each segment are chosen to yield a dispersion zero less than about 1490 nm; and
   wherein the fiber has a cabled cutoff less than or equal to about 1260 nm.

14. A method for constructing a single mode optical waveguide fiber, comprising:
   forming a central core segment having a relative index within the range of from about 0.5 3% to about 0.9%, and an outer radius within the range of from about 3.1 μm to about 5.0 μm;
   forming a first annular core segment about the central core segment, the first annular core segment having a relative index within the range of from about −0.2% to about 0.15%;
   forming a second annular core segment about the first annular core segment, the second annular core segment having a relative index within the range of from about 0.1% to about 0.4%, a center radius within the range of from about 11.69 μm to about 14.3 μm, and a width within the range of from about 0.4 μm to about 5.3 μm; and
   forming a third annular core segment about the second annular core segment, the third annular core segment having a relative index within the range of from about −0.2% to about 0%;
   wherein the radius and relative refractive index percent and the radii of each segment are chosen to yield a dispersion zero less than about 1490 nm; and
   wherein the fiber has a cabled cutoff less than or equal to about 1260 nm.

15. A single mode optical waveguide fiber comprising:

a core region having a central segment, a first annular segment and a second annular segment, each of the segments having a positive relative refractive index percent, and an inner and outer radius; and a clad layer surround and in contact with the core, the clad layer having a relative refractive index percent;

wherein the radius and relative refractive index percent and the radii of each segment are chosen to yield:
a dispersion zero less than about 1490 nm;
a dispersion slope of less than about 0.07 ps/nm2-km;
a cabled cutoff less than or equal to about 1260 nm; and
an effective area of greater than or equal to about 45 $\mu m^2$.

16. The optical waveguide fiber of claim 15, wherein the relative indices and radii are further selected to provide an attenuation in the optical waveguide fiber is less than or equal to about 0.25 dB/km.

17. The optical waveguide fiber of claim 15, wherein the relative indices and radii are further selected to provide a pin array bending loss is less than or equal to about 6 dB.

18. The optical waveguide fiber of claim 15, wherein the relative index of the central segment is within the range of about 0.53% to about 0.9%.

19. The optical waveguide fiber of claim 15, wherein the relative index of the first annular segment is less than about 0.15%.

20. The optical waveguide fiber of claim 15, wherein the relative index of the second annular segment is within the range of about 0.1% to about 0.4%.

21. The optical waveguide fiber of claim 15, wherein the outer radius of the central segment within the range of about 3.1 $\mu$m to about 5.0 $\mu$m.

22. The optical waveguide fiber of claim 15, wherein the center radius of the second annular segment is within the range of about 6.18 $\mu$m to about 7.7 $\mu$m.

23. The single mode optical waveguide fiber of claim 15, wherein the fiber has a cabled cutoff less than or equal to about 1200 nm.

24. The single mode optical waveguide fiber of claim 15, wherein the radius and relative refractive index percent and the radii of each segment are chosen to yield a dispersion zero less than about 1480 nm.

25. The single mode optical waveguide fiber of claim 15, wherein the radius and relative refractive index percent and the radii of each segment are chosen to yield a dispersion zero less than about 1450 nm.

26. The single mode optical waveguide fiber of claim 15, wherein the relative indices and radii are further selected to provide a total dispersion at 1550 nm of less than or equal to about 5.0 ps/nm-km.

27. The single mode optical waveguide fiber of claim 15, wherein the width of the second annular segment is within the range of about 0.4 $\mu$m to about 5.5 $\mu$m.

28. The single mode optical waveguide fiber of claim 15, wherein all core segments have a relative refractive index that is positive.

29. The single mode optical waveguide fiber of claim 15, wherein the relative index of the clad layer is 0%.

* * * * *